United States Patent
Bharat et al.

(10) Patent No.: US 10,143,852 B2
(45) Date of Patent: Dec. 4, 2018

(54) DETERMINATION APPARATUS FOR DETERMINING THE POSE AND SHAPE OF AN INTRODUCTION ELEMENT

(71) Applicant: KONINKLIJKE PHILIPS N.V., Eindhoven (NL)

(72) Inventors: Shyam Bharat, Cortlandt Manor, NY (US); Ehsan Dehghan Marvast, New York, NY (US); Jochen Kruecker, Washington, DC (US); Cynthia Ming-fu Kung, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 157 days.

(21) Appl. No.: 14/412,824

(22) PCT Filed: Jul. 15, 2013

(86) PCT No.: PCT/IB2013/055813
§ 371 (c)(1),
(2) Date: Jan. 5, 2015

(87) PCT Pub. No.: WO2014/013418
PCT Pub. Date: Jan. 23, 2014

(65) Prior Publication Data
US 2015/0190653 A1 Jul. 9, 2015

Related U.S. Application Data

(60) Provisional application No. 61/672,392, filed on Jul. 17, 2012.

(51) Int. Cl.
*A61N 5/10* (2006.01)
*A61B 34/20* (2016.01)
*A61B 90/00* (2016.01)

(52) U.S. Cl.
CPC ......... *A61N 5/1007* (2013.01); *A61N 5/1027* (2013.01); *A61B 2034/2051* (2016.02);
(Continued)

(58) Field of Classification Search
CPC ............ A61B 2034/2051; A61B 34/20; A61B 2090/392; A61B 2090/3958;
(Continued)

(56) References Cited

U.S. PATENT DOCUMENTS 5,391,139 A 2/1995 Edmundson
7,322,929 B2 1/2008 Lovoi
(Continued)

FOREIGN PATENT DOCUMENTS

CN 1911158 A 2/2007
EP 1745820 A1 1/2007
(Continued)

OTHER PUBLICATIONS

Alterovitz, R. et al. "Optimization of HDR brachytherapy dose distributions using linear programming with penalty costs". Medical Physics, vol. 33, No. 11, pp. 4012 to 4019, Nov. 2006.

*Primary Examiner* — Christine H Matthews

(57) ABSTRACT

The invention relates to a determination apparatus for determining the pose and shape of an introduction element like a catheter within a living being, wherein the introduction element is adapted to be used by a brachytherapy apparatus for introducing a radiation source close to a target object to be treated. A position determination element like guidewire with an electromagnetic tracking element is introduced into the introduction element such that it is arranged at different locations within the introduction element, wherein the positions of the position determination element within the introduction element are determined. The determined positions are then acquired depending on the determined positions for
(Continued)

determining the pose and shape of the introduction element within the living being. This can lead to a determination procedure with reduced user interaction, thereby simplifying the determination procedure for the user.

14 Claims, 5 Drawing Sheets

(52) U.S. Cl.
CPC . *A61B 2034/2055* (2016.02); *A61B 2090/378* (2016.02); *A61N 5/103* (2013.01); *A61N 2005/1012* (2013.01); *A61N 2005/1018* (2013.01)

(58) Field of Classification Search
CPC .......... A61N 2005/1018; A61N 5/1048; A61N 2005/1008; A61N 2005/1012; A61N 5/1007; A61N 5/1075
See application file for complete search history.

(56) References Cited

U.S. PATENT DOCUMENTS

| | | | |
|---|---|---|---|
| 7,862,498 B2 | 1/2011 | Nguyen et al. | |
| 8,145,290 B2 | 3/2012 | Kindlein | |
| 8,198,588 B2 | 6/2012 | Kornblau et al. | |
| 8,721,514 B2 | 5/2014 | Shechter | |
| 9,101,395 B2 | 8/2015 | Gutierrez et al. | |
| 9,364,685 B2* | 6/2016 | Kindlein | A61N 5/1007 |
| 2002/0026089 A1* | 2/2002 | Smith | A61N 5/1001 600/3 |
| 2006/0094923 A1* | 5/2006 | Mate | A61N 5/1014 600/3 |
| 2009/0127459 A1* | 5/2009 | Neustadter | G01T 1/2907 250/336.1 |
| 2010/0312038 A1 | 12/2010 | Shechter | |
| 2011/0166410 A1 | 7/2011 | Gutierrez et al. | |
| 2011/0288361 A1* | 11/2011 | Kindlein | A61N 5/1031 600/7 |
| 2012/0215052 A1 | 8/2012 | Kindlein et al. | |
| 2013/0102891 A1 | 4/2013 | Binnekamp et al. | |
| 2013/0204072 A1 | 8/2013 | Verard et al. | |

FOREIGN PATENT DOCUMENTS

| | | |
|---|---|---|
| JP | H07255744 A | 10/1995 |
| JP | H08302551 A | 11/1996 |
| JP | H0980638 A | 3/1997 |
| JP | 2006320590 A | 11/2006 |
| WO | 2008045812 A1 | 4/2008 |

* cited by examiner

DETERMINATION APPARATUS FOR DETERMINING THE POSE AND SHAPE OF AN INTRODUCTION ELEMENT

CROSS-REFERENCE TO PRIOR APPLICATIONS

This application is the U.S. National Phase application under 35 U.S.C. § 371 of International Application Serial No. PCT/IB2013/055813, filed on Jul. 15, 2013, which claims the benefit of U.S. Application Ser. No. 61/672,392, filed on Jul. 17, 2012. This application is hereby incorporated by reference herein.

FIELD OF THE INVENTION

The invention relates to a determination apparatus, a determination method and a determination computer program for determining the pose and shape of an introduction element like a catheter within a living being. The invention relates further to a brachytherapy apparatus, a brachytherapy method and a brachytherapy computer program for applying a brachytherapy to a target object within the living being.

BACKGROUND OF THE INVENTION

In a clinical high dose rate (HDR) brachytherapy catheters are inserted into a target object within a person, wherein through the inserted catheters radiation sources are introduced into the target object for treating the same. For determining the three-dimensional pose and shape of the catheters within the person, a user introduces sequentially a guidewire into the catheters, wherein the position of the tip of the guidewire within the respective catheter is electromagnetically tracked. The tracked position of the tip of the guidewire is acquired under the control of the user. However, since the catheters are inserted into the person to different depths, it is very difficult for the user to acquire the tracked position at appropriate locations within the respective catheter. Thus, generally unnecessary data are acquired, for instance, data corresponding to locations outside the person, which have to be identified correctly and filtered out, thereby rendering the complete procedure relatively cumbersome.

SUMMARY OF THE INVENTION

It is an object of the present invention to provide a determination apparatus, a determination method and a determination computer program for determining the pose and shape of an introduction element like a catheter within a living being, wherein the determination procedure can be simplified. It is a further object of the present invention to provide a brachytherapy apparatus, a brachytherapy method and a brachytherapy computer program for applying a brachytherapy to a target object within the living being, which use the simplified determination of the pose and shape of the introduction element.

In a first aspect of the present invention a determination apparatus for determining the pose and shape of an introduction element within a living being is presented, wherein the introduction element is adapted to be used by a brachytherapy apparatus for introducing a radiation source close to a target object to be treated within the living being, wherein the determination apparatus comprises:

a position determination unit comprising a position determination element for being introduced into the introduction element such that the position determination element is arranged at different locations within the introduction element, wherein the position determination unit is adapted to determine positions of the position determination element at the different locations within the introduction element, an acquisition unit for acquiring the determined positions of the position determination element for determining the pose and shape of the introduction element within the living being, and a control unit for controlling the acquisition depending on the determined positions.

Since the acquisition of the determined positions of the position determination element within the introduction element is controlled depending on the determined positions of the position determination element within the introduction element, the acquisition of unnecessary data, for instance of data corresponding to locations outside the living being, can be prevented. The determination apparatus can therefore allow for a determination procedure, which does not necessarily require a following data selection step, in which inappropriate data are identified and filtered out, thereby simplifying the determination procedure.

Moreover, since the data acquisition does not need to be necessarily controlled by the user, while the user introduces the position determination element into the introduction element and retracts the same from the introduction element, the determination procedure can be less cumbersome for the user and the user can focus on the introduction and retraction of the position determination element.

The introduction element is preferentially a catheter or a needle, wherein the position determination element can be inserted into the catheter or needle, respectively. Moreover, the position determination unit can be adapted to continuously determine the positions of the position determination element, while moving the position determination element within the introduction element. In particular, the position determination unit can be adapted to determine the position of the position determination element in realtime.

The acquisition unit is preferentially adapted to log, in particular, to store, the acquired determined positions for further processing. For instance, the acquired determined positions can be saved to a system disk. Alternatively or in addition, the acquired determined positions can directly be provided to, for example, a treatment planning unit of the brachytherapy apparatus.

The position determination element can be introduced into the introduction element by a user or it can automatically be introduced, while during moving the position determination element within the introduction element, the acquisition of the determined positions may be controlled depending on the determined positions.

The brachytherapy apparatus can comprise several introduction elements, wherein a user can sequentially insert the position determination element into the introduction elements for determining the poses and shapes, in particular, the three-dimensional poses and shapes, of the several introduction elements.

The radiation source can be introduced into the introduction element, of which the pose and shape within the living being has been determined, for treating the target object. The introduction element can be inserted adjacent to or into the target object for allowing the radiation source to be placed adjacent to or inside the target object, i.e. to be placed close to the target object.

In an embodiment the position determination unit is adapted to perform at least one of an electromagnetic position determination technique and an optical shape sensing position determination technique. These techniques allow determining the position of the position determination element within the introduction element relatively easily with high accuracy, thereby further improving the quality of determining the pose and shape of the introduction element within the living being.

In a preferred embodiment the position determination element comprises a longish part with a tip, wherein the position determination unit is adapted to determine the position of the tip as the position of the position determination element. The tip can be moved to the different locations within the introduction element, wherein the position of the tip at these different locations can be determined. For instance, the position determination element can be a guidewire, wherein the position of the tip of the guidewire can be electromagnetically tracked at the different locations within the introduction element.

The introduction element can be held in a template, wherein the position determination unit can be adapted to determine the positions of the position determination element within the introduction element with respect to the template. Moreover, the control unit is preferentially adapted to acquire the determined positions, which are distal to the template. The template is preferentially arranged directly adjacent the living being such that it is assumed that the determined positions of the position determination element, which are distal to the template, are within the living being. Thus, by acquiring the determined positions only, which are distal to the template, it can be ensured that substantially only positions within the living being are acquired.

For instance, if the position determination element is an optical shape sensing fiber, the control unit can be adapted to control the acquisition unit such that positions of locations, at which the position determination element is arranged, are acquired, which are distal to the template. Thus, the position determination element can be introduced into the respective introduction element, wherein during the introduction or after the position determination element has been introduced the positions of the position determination element, which are distal of the template, can be acquired, i.e. the three-dimensional pose and shape of the portion of the optical shape sensing fiber, which is distal of the template, can be acquired by optical shape sensing and used for determining the three-dimensional shape and pose of the respective introduction element.

The determination apparatus can further comprise a target object position providing unit for providing the position of the target object within the living being, wherein the control unit can be adapted to acquire the determined positions, which are within the region within the living being comprising the target object as indicated by the provided position of the target object.

The control unit can be adapted to start and stop the acquisition depending on the determined positions, in particular if the position determination element comprises a longish part with a tip which is introduced into and retracted from the introduction element, wherein the position determination unit is adapted to determine the position of the tip as the position of the position determination element. For instance, in an embodiment, if the introduction element is held in a template, the control unit can be adapted to start the acquisition, when the determined position of the position determination element becomes distal to the template, while the position determination element is introduced into the introduction element. Moreover, the control unit can be adapted to stop the acquisition, when the determined position of the position determination element becomes proximal to the template, while the position determination element is removed from the introduction element. If the determination apparatus comprises a target object position providing unit for providing the position of the target object within the living being, the control unit can be adapted to start the acquisition, when the determined position of the position determination element enters the region within the living being comprising the target object as indicated by the provided position of the target object, while the position determination element is introduced into the introduction element. Furthermore, the control unit can be adapted to stop the acquisition, when the determined position of the position determination element leaves the region within the living being comprising the target object as indicated by the provided position of the target object, while the position determination element is removed from the introduction element. This automatically ensures that only the fraction of the determined positions of the position determination element within the introduction element are acquired, which is useful for reliably determining the pose and shape of the introduction element within the living being, without requiring a person to select these useful determined positions of the position determination element.

It is further preferred that the position determination element is adapted to be introduced into the introduction element and to be then removed from the introduction element, wherein the control unit is adapted to acquire a first set of the determined positions of the position determination element, when the position determination element is introduced, i.e. during the introduction of the position determination element, and a second set of the determined positions of the position determination element, when the position determination element is removed, i.e. during the removal of the position determination element, wherein the acquisition unit is adapted to average the determined positions of the first and second sets for determining the pose and shape of the introduction element. This can lead to a further improved accuracy of the determined introduction element position.

It is also preferred that the position determination element is adapted to be introduced into several introduction elements of the brachytherapy apparatus, wherein the determination apparatus further comprises an introduction element determination unit for determining whether the position determination element is introduced into a introduction element, into which the position determination element has already been introduced, based on the already acquired determined positions of the position determination element. The determination apparatus can further comprise an output unit for outputting a signal, if the introduction element determination unit has determined that the position determination element is introduced into an introduction element, into which the position determination element has already been inserted. In particular, a warning signal like a warning message, which may be in the form of an audiovisual feedback, may be provided to a user, if the user reinserts the position determination element into a previously mapped introduction element. This can reduce the likelihood of redundant acquisitions of the determined positions of the position determination element within the introduction element, thereby allowing for a reduction of the time needed for determining the pose and shape of the introduction element within the person.

In an embodiment the position determination element is adapted to be introduced into several introduction elements of the brachytherapy apparatus, wherein the several introduction elements are held in openings of a template, wherein the positions of the openings are known, wherein the determination apparatus comprises an introduction element determination unit for determining a next introduction element, into which the position determination element is to be introduced, based on the already acquired determined positions of the position determination element and the known positions of the openings in the template holding the introduction elements, wherein the determination apparatus further comprises an output unit for outputting information indicating the determined next introduction element. Also this can reduce the likelihood of reintroducing the position determination element into an introduction element, which has already been mapped, thereby allowing for a reduction of time needed for determining the positions of the introduction elements within the living being.

In a preferred embodiment the position determination unit further comprises a position quality determination unit for determining the quality of the determined position of the position determination element within the introduction element. Preferentially, the position quality determination unit is adapted to determine the position quality based on at least one of noise in the determined position, the velocity of moving the position determination element within the introduction element and a comparison with provided reference positions. The velocity is preferentially determined based on the determined positions of the position determination element within the introduction element and the corresponding time. This allows a user, to which the determined position quality can be output, to redo the acquisition of the determined positions of the position determination element within the introduction element, if the quality of the acquired position data is too low, thereby reducing the likelihood that the brachytherapy is performed based on an inaccurately determined pose and shape of the introduction element within the living being.

In a further preferred embodiment the determination apparatus comprises a switch for providing a switch signal depending on an actuation of the switch by a user, wherein the control unit is adapted to control the acquisition depending on the switch signal. In particular, the control unit can be adapted to control the acquisition depending on the determined positions of the position determination element and depending on the switch signal. Moreover, the determination apparatus can be in a position determination mode, in which the three-dimensional shape and pose of the introduction element is determined, or in a calibration mode, in which the position determination element is used for calibration purposes, in particular, for determining the position of a template, in which the introduction element is held, with respect to a coordinate system defined by the position determination unit. In the position determination mode the control unit may control the acquisition depending on the determined positions of the position determination element and in the calibration mode the control unit may control the acquisition depending on the switch signal.

In a further aspect of the present invention a brachytherapy apparatus for applying a brachytherapy to a target object within a living being is presented, wherein the brachytherapy apparatus comprises:
  a radiation source emitting radiation for treating the target object within the living being,
  an introduction element for introducing the radiation source into the living being close to the target object,
  a determination apparatus as defined in claim 1 for determining the pose and shape of the introduction element within the living being.

In another aspect of the present invention a determination method for determining the pose and shape of an introduction element within a living being is presented, wherein the introduction element is adapted to be used by a brachytherapy apparatus for introducing a radiation source close to a target object to be treated within the living being, wherein the determination method comprises:
  determining positions of a position determination element, which is introduced into the introduction element, at different locations within the introduction element, at which the position determination element is arranged, and
  acquiring the determined positions of the position determination element for determining the pose and shape of the introduction element, wherein the acquisition is controlled depending on the determined positions.

In a further aspect of the present invention a brachytherapy method for applying a brachytherapy to a target object within a living being is presented, wherein the brachytherapy method comprises:
  inserting an introduction element into the living being close to the target object,
  determining the pose and shape of the introduction element within the living being as defined in claim 12,
  introducing a radiation source emitting radiation for treating the target object into the introduction element.

In another aspect of the present invention a determination computer program for determining the pose and shape of an introduction element within a living being is presented, wherein the introduction element is adapted to be used by a brachytherapy apparatus for introducing a radiation source close to a target object to be treated within the living being, wherein the determination computer program comprises program code means for causing a determination apparatus as defined in claim 1 to carry out the steps of the determination method as defined in claim 12, when the determination computer program is run on a computer controlling the determination apparatus.

In a further aspect of the present invention a brachytherapy computer program for applying a brachytherapy to a target object within a living being is presented, wherein the brachytherapy computer program comprises program code means for causing a brachytherapy apparatus as defined in claim 11 to carry out the steps of the brachytherapy method as defined in claim 13, when the brachytherapy computer program is run on a computer controlling the brachytherapy apparatus.

It shall be understood that the determination apparatus of claim 1, the brachytherapy apparatus of claim 11, the determination method of claim 12, the brachytherapy method of claim 13, the determination computer program of claim 13 and the brachytherapy computer program of claim 14 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
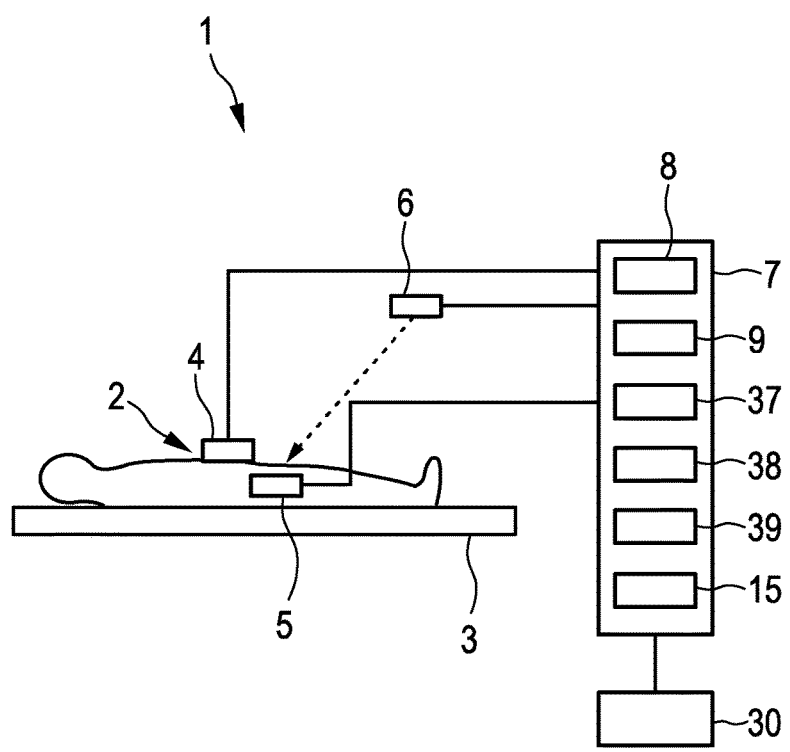
FIG. 1 shows schematically and exemplarily an embodiment of a brachytherapy apparatus for applying a brachytherapy to a target object within a living being.
Figure 2:
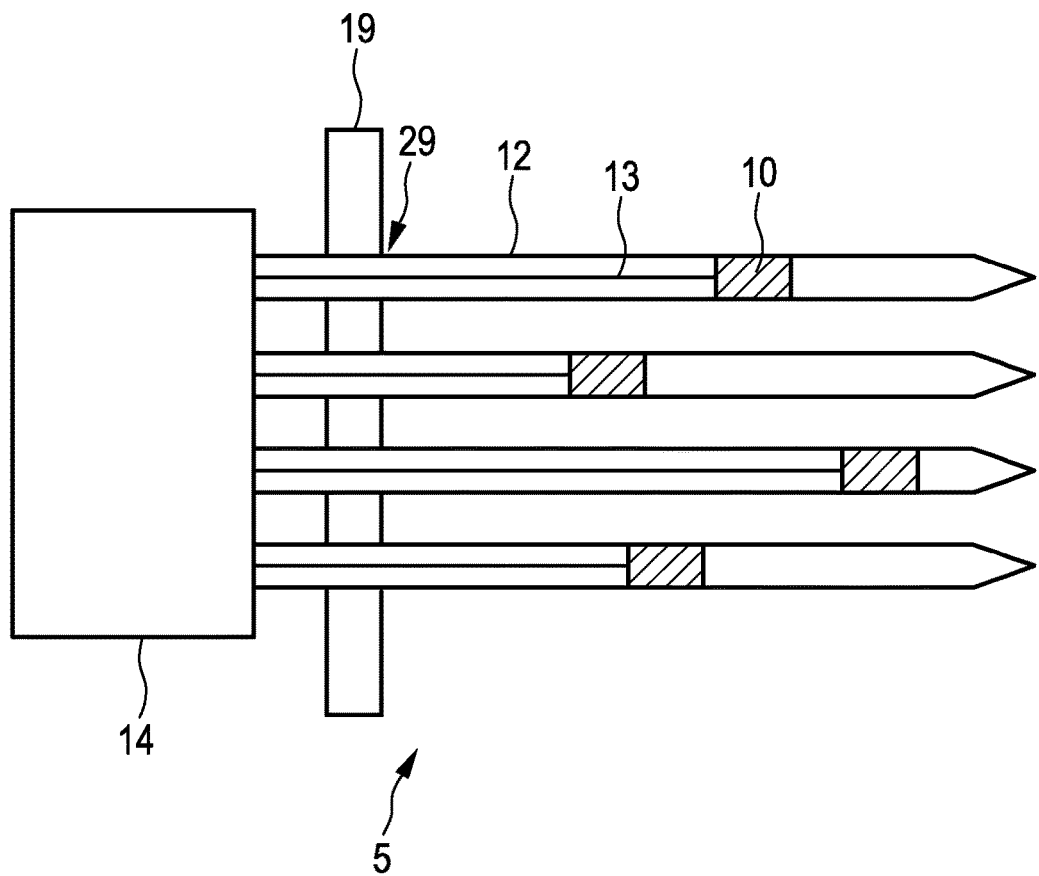
FIG. 2 shows schematically and exemplarily an embodiment of a placing unit of the brachytherapy apparatus

FIG. 1 shows schematically and exemplarily an embodiment of a brachytherapy apparatus for applying a brachytherapy to a target object within a person 2 lying on a table 3. The brachytherapy apparatus 1 comprises a placing unit 5 for being partly inserted into the person 2 and for placing radiation sources close to the target object for directing radiation emitted by the radiation sources to the target object. The placing unit 5 is exemplarily and schematically shown in more detail in FIG. 2.

The placing unit 5 comprises several introduction elements being, in this embodiment, catheters 12 for being inserted into the person 2. The placing unit 5 further comprises several navigation elements 13 being wires to which the radiation sources 10 are attached, wherein a respective wire 13 can be moved within a respective catheter 12 for placing a respective radiation source 10 at a desired placing position. The catheters 12 with the wires 13 are attached to a motor unit 14 comprising several motors for moving the wires 13 in a forward direction and in a backward direction for placing the radiation sources 10 at the desired placing positions. The radiation sources 10 are preferentially radioactive radiation sources emitting radioactive radiation like Ir-192. However, also another radioactive source can be used for performing the brachytherapy.

The placing unit 5 further comprises a template 19, which can be used for inserting the catheters 12 in a more uniform configuration into the person 2. The catheters 12 are held in openings 29 in the template 19, which are arranged in a rectangular grid.

Figure 3:
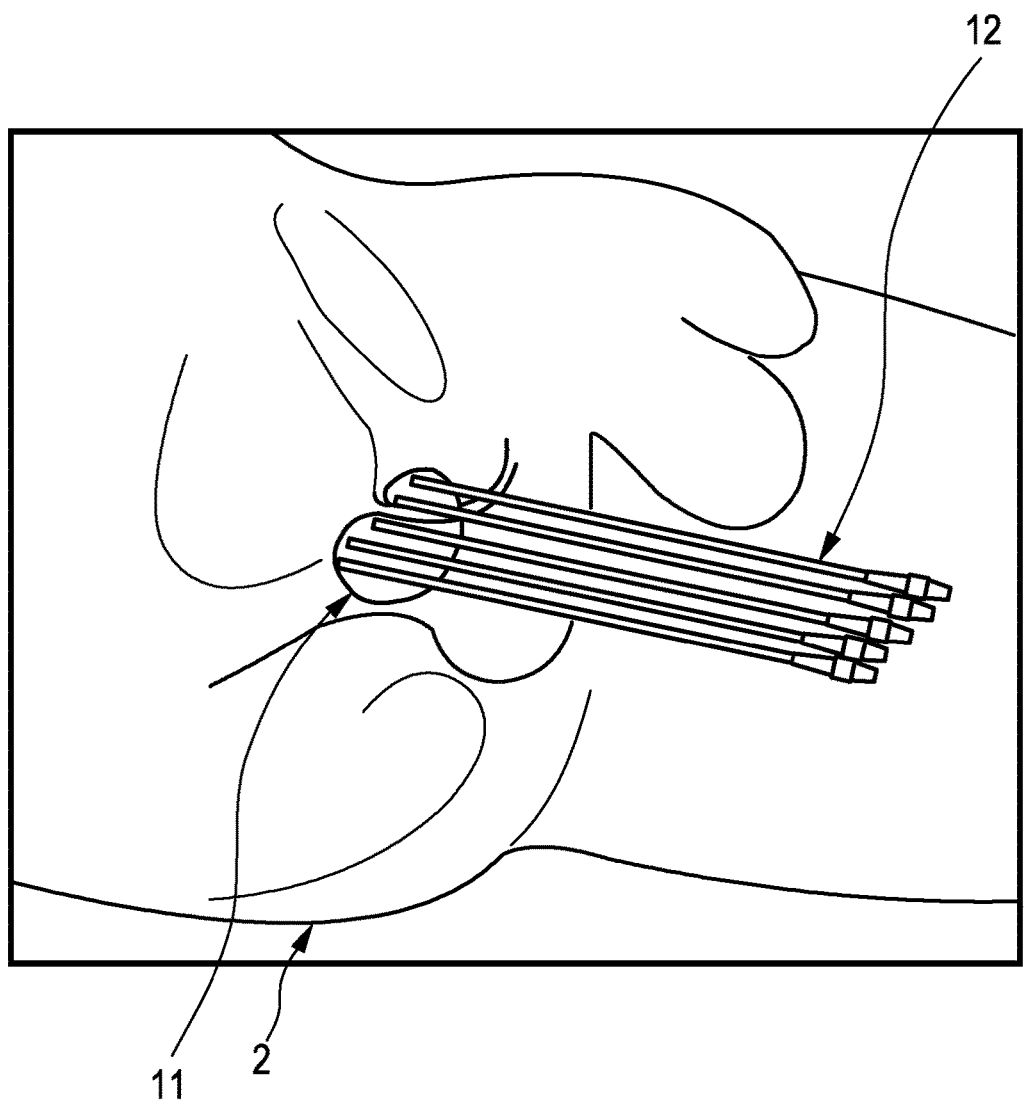
FIG. 3 shows schematically and exemplarily how catheters of the placing unit can be arranged within a prostate.
Figure 4:
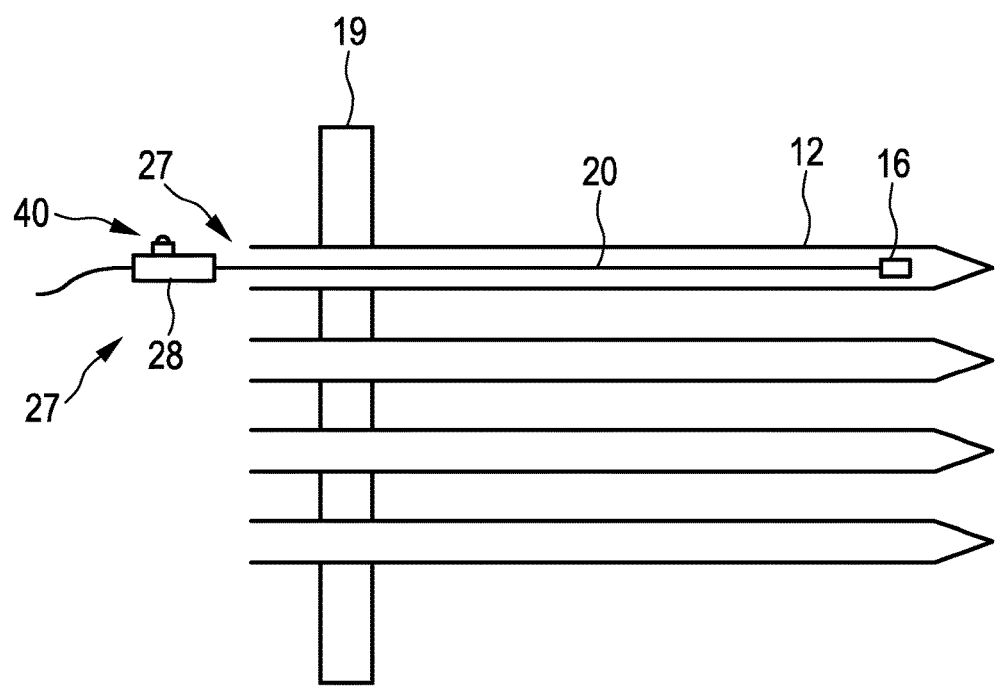
FIG. 4 shows schematically and exemplarily a position determination element being an electromagnetically tracked guidewire within a catheter.

The target object is a part of the person 2 like an organ. In this embodiment the target object is a prostate. In order to place the radiation sources close to the target object, they can be placed adjacent to or within the target object. FIG. 3 shows schematically and exemplarily a possible arrangement of the catheters 12 of the placing unit 5 within the prostate 11.

The brachytherapy apparatus 1 further comprises an imaging unit 4, 8 for generating images of the prostate 11. In this embodiment the imaging unit is an ultrasound unit 4 comprising one or several ultrasound transducers controlled by an ultrasound control unit 8 located in a processing and control device 7. The imaging unit 4, 8 is adapted to generate a three-dimensional image of the prostate 11. In other embodiments, the imaging unit can also be adapted to generate a two-dimensional image. Moreover, the imaging unit can also be adapted to generate another kind of image like a magnetic resonance image, a computed tomography image, et cetera.

The brachytherapy apparatus 1 further comprises a planning unit 39 for determining a placing plan defining placing positions at which the radiation sources 10 are to be placed and placing times defining when and how long the respective radiation source 10 is to be placed at the respective placing position based on the generated image and based on the three-dimensional poses and shapes of the catheters 12 within the person 2. Thus, the placing unit 5 is adapted to place the several radiation sources 10 at different placing positions within the prostate 11 for performing the brachytherapy, wherein the planning unit 39 is adapted to plan the different placing positions and corresponding placing times defining when and how long the respective radiation source 10 dwells at the respective placing position.

The brachytherapy apparatus 1 further comprises a control unit 15 for controlling the placing unit 5 depending on the determined placing plan. Alternatively, the placing unit 5 may be used manually in accordance with the determined placing plan, wherein a user may move the radiation sources 10 via the wires 13 within the catheters 12 in accordance with the determined placing plan.

Before introducing the radiation sources 10 into the catheters 12, the three-dimensional poses and shapes of the catheters 12 within the person 2 are determined, i.e. the three-dimensional spatial run of each catheter 12 within the person 2 is determined. For this determination procedure the brachytherapy apparatus 1 further comprises a position determination unit comprising a position determination element 27 for being sequentially introduced into the catheters 12 and for being moved to different locations within the respective catheter 12, wherein the position determination unit is adapted to determine positions of the position determination element 27 at the different locations within the respective catheter 12. In this embodiment, the position determination unit comprises an electromagnetic sensing unit 6, which cooperates with an electromagnetic sensing element 16 arranged at a tip of a guidewire 20 of the position determination element 27. The position determination element 27 can further comprise a handgrip 28 for allowing a user to introduce the position determination element 27 into the respective catheter 12 and to move the position determination element 27 within the respective catheter 12. In this way the electromagnetic sensing element 16 can be translated throughout the length of the respective catheter 12, in order to determine the three-dimensional shape and pose of the respective catheter 12. Alternatively, the position determination unit can be adapted to determine the different locations of the position determination element within the respective catheter by using optical shape sensing. In this case the position determination element comprises an optical shape sensing fiber connected to an optical shape sensing unit for determining the position of the position determination element at the different locations within the respective catheter by optical shape sensing.

The brachytherapy apparatus 1 further comprises an acquisition unit 9 for acquiring the determined positions of the position determination element 27 for determining the pose and shape of the respective catheter 12 within the person 2, and a control unit 15 for controlling the acquisition depending on the determined positions.

The position determination element 27 can be sequentially introduced into the different catheters 12 by a user or it can be automatically sequentially introduced, while during moving the position determination element 27 within the respective catheter 12 the positions of the position determination element 27 can be continuously determined, in particular, in realtime, and the acquisition of the determined positions can be controlled depending on the determined positions. Thus, although the positions of position determination element 27 within the respective catheter 12 can be continuously determined in realtime, the acquisition of these determined positions may only be performed at certain times depending on the actual determined position of the position determination element 27 within the respective catheter 12.

The acquisition unit 9 is preferentially adapted to store the acquired determined positions for further processing. The acquired determined positions can be saved to a system disc, in particular, in a user-defined format. Alternatively or in addition, the acquired determined positions can directly be provided to, for example, the planning unit 39 for allowing the planning unit 39 to plan the brachytherapy depending on the determined three-dimensional poses and shapes of the catheters 12.

The respective position of the position determination element 27 within the respective catheter 12 is preferentially determined with respect to the position of the template 19. In order to know the position of the template 19 in the coordinate system defined by the position determination unit, i.e., in this embodiment, defined by the electromagnetic tracking system, the electromagnetic sensor 16 of the position determination element 27 can be positioned at different locations on the template 19 and the positions of these locations on the template 19 can be determined, in order to determine the position of the template 19 in the coordinate system of the position determination unit. Preferentially, the electromagnetic sensor 16 is located at the openings 29 for determining the positions of these openings in the coordinate system of the electromagnetic tracking system. Also another electromagnetic sensor of the electromagnetic tracking system may be used for determining the position of the template 19 in this coordinate system. In particular, an electromagnetic sensor may be attached to the template and used for determining the position of the template in this coordinate system.

Since after this calibration step the position of the template 19 within the coordinate system defined by the electromagnetic tracking system is known, the position of the position determination unit 27 with the electromagnetic sensor 16 within the catheter 12 can be determined with respect to the position of the template 19.

In this embodiment the position determination element 27 comprises a switch 40 being arranged at the handgrip 28. The switch 40 provides a switch signal to the control unit 15 depending on an actuation of the switch 40 by a user. During the calibration step the user can actuate the switch 40, in particular press a push button of the switch 40, wherein then the control unit 15 can control the acquisition unit 9 to acquire the determined position of the electromagnetic sensor 16. The user can actuate the switch 40, when the user has located the electromagnetic sensor 16 at a desired location on the template 19, in order to ensure that the respective position is only acquired, when the electromagnetic sensor 16 has been placed at a desired location on the template 19. If instead of the position determination element 27 another element with an electromagnetic sensor, which may be regarded as being a pure calibration device, is used for performing the template calibration, also this other element may comprise a corresponding switch.

The switch 40 of the position determination element 27 can also be used during the determination and acquisition of positions of the position determination element 27 within the respective catheter 12. For this reason the switch 40 is attached at an appropriate distance to the tip of the guidewire 20, which is preferentially, flexible, so as to have a sufficient length to map the respective catheter 12. The control unit 15 can then be adapted to control the acquisition of the determined positions of the position determination element 27 within the respective catheter 12 depending on these determined positions and additionally also depending on a switch signal, which may be provided by the switch 40.

The determination apparatus can be adapted to be operable in a position determination mode, in which the three-dimensional shape and pose of the introduction element is determined, and in a calibration mode, in which the position determination element is used for calibration purposes, in particular, for determining the position of a template, in which the introduction element is held, with respect to a coordinate system defined by the position determination unit. The determination apparatus can comprise a user interface, in particular, a graphical user interface, allowing the user to select the desired mode of operation. In the position determination mode the control unit may control the acquisition depending on the determined positions of the position determination element and optionally also depending on the switch signal and in the calibration mode the control unit may control the acquisition depending on the switch signal only.

The control unit 15 can be adapted to acquire the determined positions of the position determination element 27 within the respective catheter 12, when the determined positions of the position determination element 27 are distal to the template 19. Thus, the control unit 15 can be adapted to start the acquisition, when the determined position of the position determination element 27 becomes distal to the template 19, while the position determination element 27 is introduced into the respective catheter 12. Moreover, the control unit 15 can be adapted to stop the acquisition, when the determined position of the position determination element 27 becomes proximal to the template 19, while the position determination element 27 is removed from the respective catheter 12.

The planning unit 39 can be adapted to determine the target object 11 based on the image generated by the imaging unit 4, 8, wherein the planning unit 39 can be adapted to delineate the target object 11 by applying, for instance, a segmentation algorithm to the image for completely automatically or semi-automatically delineating the target object 11 within the image generated by the imaging unit 4, 8. The planning unit 39 can also comprise a graphical user interface for allowing the user, which may be radiologist, to manually delineate the target object 11, in order to determine the target object. The imaging unit 4, 8 together with the planning unit 39 can therefore be regarded as being a target object position providing unit for providing the position of the target object 11 within the person 2, i.e. for providing the region occupied by the target object 11 within the person 2. The control unit 15 can be adapted to acquire the determined positions of the position determination element 27 within the respective catheter 12, when the determined positions of the position determination element 27 are within the region within the person 2 comprising the target object 11 as indicated by the provided target object position. In particular, the control unit can be adapted to start the acquisition, when the determined position of the position determination element 27 enters the region within the person 2 comprising the target object 11 as indicated by the provided position of the target object, while the position determination element 27 is introduced into the respective catheter 12. Furthermore, the control unit 15 can be adapted to stop the acquisition, when the determined position of the position determination element 27 leaves the region within the person 2 comprising the target object 11 as indicated by the provided position of the target object 11, while the position determination element 27 is removed from the respective catheter 12.

The planning unit 39 can also be adapted to determine the axial image plane of the image provided by the imaging unit 4,8 that corresponds to the proximal extent of the target object 11 and to relate this proximal position of the target object to the position of the template, wherein the acquisition of the determined positions of the position determination element 27 can be activated, if the determined position of the position determination element 27 is distal to the template and if the distance to the template is larger than the distance of the proximal position of the target object 11, i.e. of the determined axial image plane, to the template 19. For registering the imaging unit 4, 8 with the position determination unit, in particular, with the electromagnetic tracking system, the position determination element can be placed at several reference locations of the imaging unit 4, 8, wherein the spatial relation between the reference locations of the imaging unit 4, 8 and the image generated by the imaging unit 4, 8 is known and wherein the positions of the position determination element at the reference locations within the coordinate system of the position determination unit, in particular, of the electromagnetic tracking system, are determined.

The position determination element 27 can be introduced into the respective catheter 12 and then be withdrawn from the respective catheter 12, wherein the control unit 15 can be adapted to control the acquisition unit 9 to acquire a first set of the determined positions of the position determination element 27 during the introduction and a second set of the determined positions of the position determination element 27 during the removal, wherein the acquisition unit 9 can be adapted to average the determined positions of the first and second sets for determining the pose and shape of the respective catheter 12. For instance, the first set of determined positions can define a first shape and pose of the respective catheter 12, i.e. a first spatial run, within the person 2 and the second set of the determined positions can define a second pose and shape of the respective catheter 12, i.e. a second spatial run, within the person 2, wherein these two spatial runs, i.e. the corresponding lines or curves, can be averaged for determining the position, i.e. the spatial run, of the respective catheter within the person 2. Thus, the obtained positional data can be separated into two sets of data for the guidewire moving into and out of the respective catheter, wherein these two sets of data can be averaged, in order to obtain a consolidated catheter position.

The brachytherapy apparatus 1 further comprises an introduction element determination unit 37 for determining whether the position determination element 27 is introduced into a respective catheter 12, into which the position determination element 27 has already been introduced, based on the already acquired determined positions of the position determination element 27. If the introduction element determination unit 37 determines that the position determination element 27 is introduced into a catheter 12, into which the position determination element 27 has already been introduced, an output unit 30 of the brachytherapy apparatus can output a signal. In particular, warning messages in the form of audiovisual feedbacks can be relayed to the user, if the user reinserts the guidewire, i.e. the position determination element 27, into a catheter 12 that has already been mapped. For determining whether the position determination element 27 is introduced into a catheter 12, into which the position determination element 27 has already been introduced, the introduction element determination unit 37 can comprise a virtual binary grid, which comprises openings that correspond to the openings 29 of the template 19. Each position in the binary grid, which corresponds to an opening 29 of the template 19, can have two values, a first value indicating that the catheter 12 held in the respective opening 29 has already been mapped and a second value indicating that a catheter 12 held in the respective opening 29 has not been mapped. If a user starts to introduce the position determination element 27 into a certain catheter 12, the introduction element determination unit 37 can determine to which opening 29 in the template 19 the catheter 12, into which the position determination element 27 is introduced, relates based on the determined position of the position determination element 27. If to the corresponding position in the virtual binary grid a second value has been assigned, the respective catheter 12 has not already been mapped and, thus, the output unit 30 does not output a warning message. If to the corresponding position in the virtual binary grid the first value has been assigned, the respective catheter 12 has already been mapped and a warning message is output by the output unit 30. After a respective catheter 12 has been mapped, i.e. after the pose and shape of the respective catheter 12 within the person 2 has been determined, the virtual binary grid is updated by assigning to the corresponding position of the virtual binary grid the first value. Thus, if a catheter is mapped with a guidewire, i.e. with the position determination element, the virtual binary grid can be updated to reflect this by changing the binary value for the grid hole, i.e. for the template opening, through which the respective catheter has been inserted into the person.

The introduction element determination unit 37 is further adapted to determine a next catheter, into which the position determination element 27 is to be introduced, based on the already acquired determined positions of the position determination element 27 and the known positions of the openings 29 in the template 19 holding the catheters 12, wherein the output unit 30 can be adapted to output information indicating the determined next catheter. In particular, an audiovisual feedback can be provided to guide the user to the next catheter that has not been mapped yet. For instance, the introduction element determination unit 37 can be adapted to show the virtual binary grid on a display of the output unit 30 and to indicate a certain position, which corresponds to a catheter that has not already been mapped, by a certain intensity or color. The introduction element determination unit 37 can be adapted to determine the next catheter as being the catheter being closest to the last catheter that has been mapped. If during the grid calibration only the position of the template in the coordinate system of the position determination unit, in particular, of the electromagnetic tracking system, is determined, without defining which openings of the template hold a catheter, this additional information can be provided by a user to the introduction element determination unit 37 via a user interface like a keyboard, a mouse, a touch screen, et cetera. For instance, the virtual grid can be shown on the output unit 30 and a user can indicate the openings holding a catheter via the user interface.

The brachytherapy apparatus 1 further comprises a position quality determination unit 38 for determining the quality of the determined position of the position determination element 27 within the respective catheter 12. Preferentially, the position quality determination unit 38 is adapted to determine the position quality based on at least one of the noise in the determined position, the velocity of moving the position determination element 27 within the respective catheter 12 and a comparison with provided reference positions. In particular, the acquired electromagnetic mapping data, or in another embodiment the acquired optical mapping data in the case of optical shape sensing, can be checked for accuracy in realtime, wherein a feedback about the quality can be provided to the user, for instance, in order to request a reacquisition, if the accuracy is considered as being insufficient.

For determining the position quality based on the noise, the root mean square noise level of the acquired electromagnetic mapping data can be determined, wherein, if the root mean square noise level is above a predefined noise threshold value, the position quality is regarded as being too low and corresponding position quality information can be output to the user by the output unit 30. The predefined noise threshold value for comparing the root mean square noise level can be determined by calibration measurements. If the position quality determined by using the noise is too low, the information output by the output unit 30 can request the user to reacquire the positions of the position determination element 27 and/or suggest potential solutions for reducing the noise like repositioning of an electromagnetic field generator relative to a stepper of the electromagnetic tracking system being, in this embodiment, the position determination unit.

For determining the position quality depending on the velocity of moving the position determination element 27 within the respective catheter 12 the time can be measured, in which the positions of the position determination element 27 are determined. This velocity can be determined while the guidewire, i.e. the position determination element 27, is inserted and/or while it is pulled back. Since the rate of determining the position of the position determination element 27 within the catheter 12 is limited, a relatively fast motion of the position determination element 27 within the respective catheter 12 leads to a relatively sparse spatial sampling of the positions of the position determination element 27 within the respective catheter. Moreover, a very fast motion of the position determination element 27 within the respective catheter 12 can lead to dropouts of the electromagnetic signal. Corresponding velocity threshold values can be predefined, wherein, if the velocity of the movement of the position determination element 27 within the respective catheter 12 is not in between these velocity threshold values, it can be indicated to the user via the output unit 30 that the position quality is too low. In this case information can be output to the user suggesting a reacquisition of the mapping data, i.e. of the positions of the position determination element 27 within the respective catheter.

For determining the position quality depending on a comparison with provided reference positions the acquired mapping data, i.e. the acquired determined positions of the position determination element within the respective catheter, can be matched with a previously carried out grid calibration, i.e. the above described template calibration, wherein the grid calibration is obtained by using the electromagnetic tracking data acquired at the surface of the template. Since the position determination element, in particular, the guidewire, is inserted through the template, the acquired determined positions of the position determination element also include some data points from the surface of the template. If these data points differ from the data points acquired during the grid calibration, for instance, if a corresponding deviation is larger than a predefined threshold value, the position quality can be regarded as being too low and the output unit 30 may output a warning message to the user. The position quality determination unit 38 and the output unit 30 can also be adapted to output suggestions for improving the position quality to the user like a) updating the grid calibration by using the new data points actually acquired while the position determination element has been inserted into the respective catheter through the template, b) redoing the grid calibration or c) reacquiring the determined positions of the position determination element by again introducing the position determination element into the respective catheter.

The acquisition unit 9 can be adapted to automatically save the acquired data for each catheter to a system disk in any format as desired by the user. Storing the acquired data, i.e. the acquired determined positions of the position determination element within the respective catheter, may be desirable, if the planning unit of the brachytherapy apparatus is arranged at a different location. The saved catheter position data may then be transferred via an intranet or by using another data transfer mechanism to the planning unit. The determined catheter positions may also be directly fed into the planning unit. This option may be desirable, if the units for determining the pose and shape of the respective catheter and the planning unit are part of the same brachytherapy apparatus as described above with reference to FIG. 1.

The position determination unit 6, 27, the acquisition unit 9, and the control unit 15 can be regarded as being parts of a determination apparatus for determining the pose and shape of a catheter within the person. In the embodiment described above with reference to FIG. 1 the determination apparatus is integrated in the brachytherapy apparatus. In another embodiment, the determination apparatus can also be a separate apparatus, which determines the pose and shape of the respective catheter within the person, wherein the determined poses and shapes of the catheters can be provided to a separate brachytherapy apparatus for allowing the brachytherapy apparatus to plan the brachytherapy based on the determined poses and shapes of the catheters 12 within the person 2.

The planning unit 39 can be adapted to determine inter-catheter spacings between neighboring catheters 12 based on the determined poses and shapes of the catheters 12 and to determine the placing plan depending on the determined inter-catheter spacings. Moreover, the planning unit 39 can be adapted to determine a spatial relationship between the catheters 12 and the target object 11 based on the determined poses and shapes of the catheters 12 and based on the image of the target object 11 generated by the imaging unit 4, 8 and to determine the placing plan further depending on the determined spatial relationship between the catheters 12 and the target object 11. For example, the planning unit 39 can be adapted to determine the pose and shape of each catheter 12 relative to the target object 11 and to use these determined poses and shapes for generating the placing plan. For planning the different placing positions and corresponding placing times known planning techniques can be used like the planning technique disclosed in the article "Optimization of HDR brachytherapy dose distributions using linear programming with penalty costs" by Ron Alterovitz et al., Medical Physics, volume 33, number 11, pages 4012 to 4019, November 2006.

Figure 5:
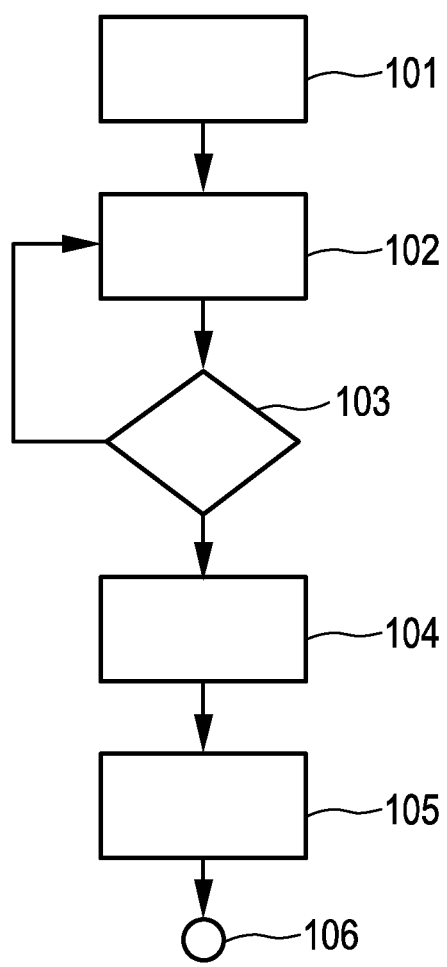
FIG. 5 shows a flowchart exemplarily illustrating an embodiment of a brachytherapy method for applying a brachytherapy to a target object within a living being.

In the following an embodiment of a brachytherapy method for applying a brachytherapy to a target object within a living being will exemplarily be described with reference to a flowchart shown in FIG. 5.

In step 101 an initial image is generated by the imaging unit, wherein the generated image shows the target object within the patient. Moreover, the template is placed adjacent to the person such that the catheters can be introduced through the openings in the template into the target object, wherein then the catheters are inserted into the person into the target object through the openings in the template. In particular, the catheters are inserted through the openings in the template into the prostate of the person. In step 102 the position determination element is introduced into one of the inserted catheters, wherein during this introduction of the position determination element the position determination element is moved along different locations within the catheter and the positions of the position determination element at the different locations are determined by the position determination unit. This determination of the positions of the position determination element during the introduction of the position determination element into the catheter is preferentially performed in realtime. Preferentially, also during removing the position determination element from the catheter the positions of the position determination element within the catheter are determined in realtime by the position determination unit. At least some of the determined positions are acquired by the acquisition unit, wherein the acquisition is controlled depending on the determined positions. The acquisition of the determined positions of the position determination element includes, for instance, storing the determined positions in a storing unit of the acquisition unit for further processing. The acquisition can be performed such that, for example, the determined positions are only acquired, if they are located within the target object or if they are located distal to the template. The acquired determined positions are then used to determine the pose and shape of the catheter within the person. For instance, the acquired determined positions, which are arranged along a line describing the pose and shape of the catheter, can directly define the pose and shape of the catheter such that the sequence of acquired determined positions of the position determination element can directly be regarded as being the determined pose and shape of the catheter. Alternatively, determined positions, which have been acquired while the position determination element has been introduced into the catheter, and determined positions, which have been acquired while the position determination element has been removed from the catheter, can be averaged for determining the pose and shape of the catheter. The determined pose and shape of the catheter can be stored in a storing unit and/or transmitted to a planning unit.

In step 103 it is checked whether the poses and shapes of all catheters inserted into the person have been determined already, wherein, if this is the case, the brachytherapy method continues with step 104. If there are still catheters inserted into the person, of which the pose and shape has not been determined, the pose and shape of this catheter is determined in step 102. Thus, sequentially the poses and shapes of all catheters inserted into the person are determined, whereupon the brachytherapy method continues with step 104.

In step 104 the planning unit plans the brachytherapy, i.e. the introduction of radiation sources into the catheters, depending on the determined poses and shapes of the catheters. In particular, the planning unit determines a placing plan defining placing positions, at which the radiation sources are to be placed, and placing times defining how long the respective radiation source should be placed at a respective placing position. In step 105 the brachytherapy is performed in accordance the placing plan determined in step 104. In particular, the radiation sources are moved to placing positions within the catheters and remain for certain placing times at the placing positions in accordance with the placing plan. The brachytherapy method ends in step 106.

The determinations of the positions of the position determination element and the acquisition of the determined positions of the position determination element depending on the determined positions for determining the pose and shape of the respective catheter within the person as described above with reference to step 102 can be regarded as defining a determination method for determining the pose and shape of a catheter within the person.

The brachytherapy apparatus is preferentially adapted to perform a HDR brachytherapy as a form of cancer therapy that utilizes high doses of ionizing radiation delivered over a short period of time in the order of some minutes directly at or near the target. Due to the high dose rate delivery rates involved the margin of error is minimal. The ability to accurately identify catheter positions prior to treatment planning is important for developing a high quality plan. Subsequent to treatment planning, it may be useful to track catheter motion, in particular, relative to the target, not just between treatment planning and delivery, but also during treatment delivery.

Although in an above described embodiment shown in FIG. 3 the arrangement of catheters is implanted transperineally in the prostate, in other embodiments the arrangement of catheters can also be implanted differently into the prostate. Moreover, in other embodiments the catheters may not be implanted in the prostate, but in another target object like another organ for treating the organ, in particular, for destroying a tumor in the organ.

Although in an above described embodiment the ultrasound unit is adapted to be placed on the outer skin of the person for generating the ultrasound images, in other embodiments the imaging unit can also be another kind of ultrasound imaging unit. For example, the imaging unit can comprise a trans-rectal ultrasound (TRUS) probe for generating the ultrasound images. The imaging unit can also be another imaging modality like a magnetic resonance imaging modality, a computed tomography imaging modality, et cetera.

The catheter identification process, i.e. the process of detecting the pose and shape of the catheter within the person, which is preferentially used in a clinical HDR brachytherapy procedure, preferentially involves the introduction of a tracked guidewire, i.e. of the position determination element, sequentially into each implanted catheter. The position data acquisition, which in this example is an electromagnetic data acquisition, can be started and stopped at appropriate positions of the tracked guidewire tip, in order to completely delineate each catheter. If this were to be done manually, for instance, via a software interface, repeatability in this process might be hard to achieve, because each catheter is inserted to a different depth, thus resulting in data that might be hard to interpret. Additionally, the workflow might also be cumbersome, with the need to simultaneously insert the guidewire in the catheters and interact with the system software to ensure appropriate data acquisition.

The brachytherapy apparatus described above with reference to FIGS. 1 to 4 provides therefore preferentially an automatic acquisition of electromagnetic catheter mapping data, based on the known realtime position of the tracked guidewire tip with respect to the surface of the template, which could also be named grid. The brachytherapy apparatus preferentially only requires the user to sequentially insert the tracked guidewire in each of the implanted catheters. No additional user-system interaction may be necessary. Thus, the workflow can be made simpler with reduced manual interaction with the brachytherapy apparatus. The accuracy and repeatability of data acquisition can also be improved.

Although in the above described embodiments mainly the use of electromagnetic tracking technology is described, the pose and shape of the catheter can also be determined by using another tracking technology for tracking the position determination element within the respective catheter like optical shape sensing. For instance, if the position determination unit is adapted to determine the position of the position determination element within the respective catheter by optical shape sensing, the position of the template with respect to the coordinate system of the optical shape sensing tracking system can be determined by placing the position determination element at different locations on the template as described above with respect to the calibration performed by using the electromagnetic tracking system. In particular, in this example preferentially the tip of the position determination element is placed at the respective location on the template, whereupon the position of the tip is determined by using optical shape sensing. Thus, also if the position determination unit is adapted to use optical shape sensing for determining the position of the position determination element within the respective catheter, the position of the position determination element can be determined with respect to the template. Moreover, also in the case of optical shape sensing the control unit is preferentially adapted to control the acquisition unit such that positions of locations, at which the position determination element is arranged, are acquired, which are distal to the template, i.e. which are inside the person if the template is arranged directly adjacent the person. Thus, for instance, the position determination element can be introduced into the respective catheter, wherein during the introduction or after the position determination element has been introduced the positions of the position determination element, which are distal of the template, can be acquired, i.e. the three-dimensional pose and shape of the portion of the position determination element, which is distal of the template, can be acquired by optical shape sensing and used for determining the three-dimensional shape and pose of the respective catheter.

Although in above described embodiments the poses and shapes of catheters are determined, in other embodiments the brachytherapy apparatus and the determination apparatus can be adapted to detect the pose and shape of another kind of introduction element for introducing a radiation source into the person. For instance, also a needle can be used as an introduction element, wherein the position determination element can be introduced into the needle for determining the position of the needle within the person. In particular, a hollow needle can be used for placing a radiation source into the living being, wherein the three-dimensional shape and pose can be determined by introducing the position determination element into the needle. Moreover, although in above described embodiments the brachytherapy is a HDR brachytherapy, the brachytherapy can also be a low dose rate (LDR) brachytherapy.

Although in the above described embodiments the brachytherapy apparatus and the determination apparatus are used in a brachytherapy procedure applied to a target object within a person, the brachytherapy apparatus and the determination apparatus can also be adapted to provide a brachytherapy procedure that can be applied to a target object in an animal.

In known clinical HDR brachytherapy procedures the catheter identification process is done manually on TRUS images. This is not only error-prone, but also very time consuming. The automated catheter mapping method described above with reference to FIGS. 1 to 5 can significantly reduce the time taken for this step and also results in an easy and seamless workflow. Preferentially, the user, which is preferentially a clinician, only has to sequentially insert the tracked guidewire in each implanted catheter, a process that may only take about two to three minutes. From the time span of 30 to 45 minutes that it currently takes in the clinic to delineate catheters manually on TRUS images, this represents a huge improvement in workflow and time savings.

Also, since the data acquisition is preferentially started and stopped automatically, no additional user effort is preferentially needed to prune the recorded data prior to using it for treatment planning. Thus, there is preferentially no additional overhead between the catheter identification and treatment planning procedures, which may result in further time savings.

In the embodiments described above with reference to FIGS. 1 to 4 the three-dimensional poses and shapes of the catheters within the person are tracked by the electromagnetic tracking system and used for treatment planning. In order to have catheter poses and shapes and the template in the same coordinate system, the relation between the grid, i.e. the template, and the electromagnetic tracking coordinate system is identified during a preoperative calibration phase, termed "grid calibration", which has been described above.

As has been described above, the grid calibration can be performed by using the position determination element, which may substantially be a guidewire with an electromagnetic sensing element at its tip. However, as also described above, also another electromagnetically tracked device may be used for performing the grid calibration. This other device, which can be regarded as being a calibrator device, can house the electromagnetically tracked sensing element. It comprises preferentially a flexible guidewire with an electromagnetic sensor embedded at its tip. The calibrator device can further comprise a push-button switch connected to a computer system, for instance, connected to the acquisition unit of the brachytherapy apparatus or to another acquisition unit, wherein the respective position of the electromagnetic sensing element is acquired, if the user presses the button when the electromagnetic sensing element is inside a grid hole for data collection. This will reduce the number of incorrect grid point acquisitions and, thus, decreasing the procedure time in comparison to known grid calibration techniques, in which the position is acquired after two to five seconds of immobility, because in the latter case, when the user's hand motion stops for a few seconds in the electromagnetic field of view, while the calibrator device is out of a grid hole, i.e. out of an opening of the template, the data will be recorded and erroneously assumed as the position of a grid hole. In this case, a repetition calibration would be necessary.

Also the position determination element, for instance, the electromagnetically tracked guidewire for determining the shape and pose of the respective catheter within the person can comprise a push button switch as described above with reference to FIG. 4, wherein the acquisition unit can be adapted to acquire the determined position depending on a switch signal, which depends on whether the push-button switch is activated or not and depending on the actually determined position of the position determination element within the respective catheter. For instance, the acquisition unit can be adapted to acquire the determined positions of the position determination element within the respective catheter, if i) the tip of the position determination element is within the target object or at least distal to the template and ii) the push-button switch is actuated by the user. Thus, also the push-button switch can be used by the user to indicate a start or a stop of the acquisition of determined positions of the position determination element.

The switch can be a push-button switch which may function in different ways. For instance, it can work in a transient mode, wherein a single button press may activate the data acquisition depending on the determined positions of the position determination element within the respective catheter for a short time period of, for instance, one to two seconds. The push-button switch may also be operated in toggle mode, wherein a single button press may either start or stop the position dependent data acquisition. The switch can also be another switch comprising, for instance, a sliding mechanism, wherein two positions can be provided for the switch, one to activate the position dependent acquisition and another to stop the position dependent acquisition.

The brachytherapy apparatus and the determination apparatus preferentially introduce a complete automation in the catheter tracking work flow, which is preferentially electromagnetically based. Catheter identification, mapping and saving of position data can be done automatically, which may result in an improved and streamlined workflow with significant time savings.

For determining the pose and shape of the catheters within the person during a clinical HDR brachytherapy procedure the position determination element, in particular, the electromagnetically tracked guidewire, is preferentially sequentially inserted into each implanted catheter. The brachytherapy apparatus and the determination apparatus are preferentially adapted such that the position data, in particular, the electromagnetic catheter mapping data, are automatically acquired based on the knowledge about the realtime position of the position determination element, in particular, of the tracked guidewire tip, with respect to a surface of the template and/or the proximate extend of the target object, which may be the prostate. Preferentially, the brachytherapy apparatus and the determination apparatus only require the user to sequentially insert the position determination element in each of the implanted catheters, wherein the catheter mapping data, i.e. suitable determined positions of the position determination element within the respective catheter, are acquired and stored automatically. An additional user-system interaction is preferentially not necessary. Optionally, this automatic mapping procedure is only performed, if a switch at the position determination element is actuated such that a corresponding switch signal indicates to the control unit that the automatic catheter mapping should be performed. In addition to the automatic position data acquisition the brachytherapy apparatus and the determination apparatus can also be adapted to warn the user, for instance, via messages on a screen and/or via audible beeps, if the user reinserts the position determination element in a catheter that has already been mapped, i.e. of which the pose and shape and, thus, the position has already been determined. The acquired data can automatically be saved to a disk in a user desired format. Alternatively, a direct interface with a planning unit of the brachytherapy apparatus can also be used for directly providing the acquired data to the planning unit.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the three-dimensional pose and shape of the introduction element within the living being or like the determination of the placing plan performed by one or several units can be performed by any other number of units or devices. The determinations and/or the control of the determination apparatus in accordance with the determination method and/or the control of the brachytherapy apparatus in accordance with the brachytherapy method can be implemented as program code means of computer program and/or dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a determination apparatus for determining the pose and shape of an introduction element like a catheter within a living being, wherein the introduction element is adapted to be used by a brachytherapy apparatus for introducing a radiation source close to a target object to be treated. A position determination element like guidewire with an electromagnetic tracking element is introduced into the introduction element such that it is arranged at different locations within the introduction element, wherein the positions of the position determination element within the introduction element are determined. The determined positions are then acquired depending on the determined positions for determining the pose and shape of the introduction element within the living being. This can lead to a determination procedure with reduced user interaction, thereby simplifying the determination procedure for the user.

The invention claimed is:

1. A determination apparatus for determining a pose and shape of an introduction element within a living being, wherein the introduction element is adapted to be used by a brachytherapy apparatus for introducing a radiation source close to a target object to be treated within the living being, the determination apparatus comprising:
   a position determination unit that includes a position determination element for being introduced into the introduction element, wherein the position determination unit is adapted to continuously determine, in real-time, positions of the position determination element at different locations within the introduction element, at which the position determination element is arranged;
   a data acquisition unit for acquiring only a fraction of the continuously determined positions of the position determination element at the different locations within the introduction element, wherein the data acquisition unit comprises a system disk configured to store the acquired fraction of determined positions for use in determining the pose and shape of the introduction element within the living being based on the acquired fraction of determined positions; and
   a controller for controlling the data acquisition unit to only acquire and store the fraction of determined positions based on select ones of the determined positions of the position determination element in real-time at the different locations within the introduction element that correspond with (i) only locations within both the introduction element and the living being and (ii) not locations that are still within the introduction element but outside the living being.

2. The determination apparatus as defined in claim 1, wherein the position determination unit is adapted to perform at least one of an electromagnetic position determination technique and an optical shape sensing position determination technique.

3. The determination apparatus as defined in claim 1, wherein the position determination element comprises a longish part with a tip, wherein the position determination unit is adapted to determine a position of the tip as the position of the position determination element.

4. The determination apparatus as defined in claim 1, wherein the introduction element is held in a template, and wherein the controller is adapted to control the data acquisition unit, to acquire and store the fraction of determined positions which are distal to the template.

5. The determination apparatus as defined in claim 1, further comprising:
   a target object position providing unit for providing a position of the target object within the living being, wherein the controller is adapted to control the data acquisition unit to acquire and store the fraction of determined positions which are within a region of the living being that comprises the target object as indicated by the provided position of the target object.

6. The determination apparatus as defined in claim 1, wherein the position determination element is adapted to be introduced into the introduction element and then subsequently removed from the introduction element, wherein the controller is further adapted to control the data acquisition unit to acquire and store (i) a first set of the fraction of determined positions in response to the position determination element being introduced into the introduction element, and (ii) a second set of the fraction of determined positions in response to the position determination element being removed from the introduction element, and wherein the controller is further adapted to average the fraction of determined positions of the first and second sets for determining the pose and shape of the introduction element.

7. The determination apparatus as defined in claim 1, further comprising:
   a switch, subject to a user actuation, for providing a switch signal, wherein the controller is further adapted to control the data acquisition unit in response to the switch signal.

8. A brachytherapy apparatus including the determination apparatus as defined in claim 1 for determining the pose and shape of the introduction element within the living being, the brachytherapy apparatus for applying a brachytherapy to the target object within the living being, the brachytherapy apparatus comprising:
   a radiation source emitting radiation for treating the target object within the living being; and
   the introduction element for introducing the radiation source into the living being close to the target object.

9. A non-transitory computer readable medium embodied with a computer program for determining the pose and shape of an introduction element within a living being, wherein the introduction element is adapted to be used by a brachytherapy apparatus for introducing a radiation source close to a target object to be treated within the living being, the computer program comprising executable program code for causing a determination apparatus as defined in claim 1 to determine the pose and shape of the introduction element within the living being, when the computer program is executed on a computer controlling the determination apparatus.

10. A non-transitory computer readable medium embodied with a computer program for applying a brachytherapy to a target object within a living being, the computer program comprising executable program code for causing a brachytherapy apparatus as defined in claim 8 to carry out steps, when the computer program is executed on a computer controlling the brachytherapy apparatus, the steps comprising:
   inserting an introduction element into the living being close to the target object,
   determining the pose and shape of the introduction element within the living being, and
   introducing a radiation source emitting radiation for treating the target object into the introduction element.

11. A determination apparatus for determining a pose and shape of an introduction element within a living being, wherein the introduction element is adapted to be used by a brachytherapy apparatus for introducing a radiation source close to a target object to be treated within the living being, the determination apparatus comprising:
   a position determination unit that includes a position determination element for being introduced into the introduction element and arranged at different locations within the introduction element, wherein the position determination unit is adapted to continuously determine positions of the position determination element in real-time at the different locations within the introduction element;
   a data acquisition unit for acquiring only a fraction of the continuously determined positions of the position determination element at the different locations within the introduction element, wherein the data acquisition unit comprises a system disk configured to store the acquired fraction of determined positions for use in determining the pose and shape of the introduction element within the living being based on the acquired fraction of determined positions; and
   a controller for controlling the data acquisition unit to acquire and store the fraction of determined positions in response to the determined positions of the position determination element in real-time at the different locations within the introduction element that comprise (i) only locations within the living being and (ii) not locations outside the living being, wherein the position determination element is adapted to be sequentially introduced into each of a plurality of introduction elements of the brachytherapy apparatus, the determination apparatus further comprising:
   an introduction element determination unit for determining whether the position determination element is introduced into an introduction element of the plurality of introduction elements, into which the position determination element has already been introduced, based on the acquired determined positions of the position determination element.

12. A determination apparatus for determining a pose and shape of an introduction element within a living being, wherein the introduction element is adapted to be used by a brachytherapy apparatus for introducing a radiation source close to a target object to be treated within the living being, the determination apparatus comprising:
   a position determination unit that includes a position determination element for being introduced into the introduction element and arranged at different locations within the introduction element, wherein the position determination unit is adapted to continuously determine positions of the position determination element in real-time at the different locations within the introduction element;

a data acquisition unit for acquiring only a fraction of the continuously determined positions of the position determination element at the different locations within the introduction element, wherein the data acquisition unit comprises a system disk configured to store the acquired fraction of determined positions for use in determining the pose and shape of the introduction element within the living being based on the acquired fraction of determined positions; and a controller for controlling the data acquisition unit to acquire and store the fraction of determined positions in response to the determined positions of the position determination element in real-time at the different locations within the introduction element that comprise (i) only locations within the living being and (ii) not locations outside the living being, wherein the position determination element is adapted to be introduced into several introduction elements of the brachytherapy apparatus, wherein the several introduction elements are held in openings of a template, wherein positions of the openings are known, the determination apparatus further comprising:

an introduction element determination unit for determining a next introduction element of the several introduction elements, into which the position determination element is to be introduced, based on the acquired determined positions of the position determination element and the known positions of the openings in the template holding the several introduction elements; and an output unit for outputting information to indicate the determined next introduction element.

13. A determination apparatus for determining a pose and shape of an introduction element within a living being, wherein the introduction element is adapted to be used by a brachytherapy apparatus for introducing a radiation source close to a target object to be treated within the living being, the determination apparatus comprising:

a position determination unit that includes a position determination element for being introduced into the introduction element and arranged at different locations within the introduction element, wherein the position determination unit is adapted to continuously determine positions of the position determination element in real-time at the different locations within the introduction element;

a data acquisition unit for acquiring only a fraction of the continuously determined positions of the position determination element at the different locations within the introduction element, wherein the data acquisition unit comprises a system disk configured to store the acquired fraction of determined positions for use in determining the pose and shape of the introduction element within the living being based on the acquired fraction of determined positions; and a controller for controlling the data acquisition unit to acquire and store the fraction of determined positions in response to the determined positions of the position determination element in real-time at the different locations within the introduction element that comprise (i) only locations within the living being and (ii) not locations outside the living being, wherein the position determination unit further comprises a position quality determination unit, wherein the position quality determination unit is configured to determine a quality of a determined position of the position determination element within the introduction element in response to at least one of (i) a noise in the determined position, (ii) a velocity of the position determination element moving within the introduction element, and (iii) a comparison with reference positions, the determination apparatus further comprising:

an output unit configured to output feedback to provide at least an indication in response to a determined quality of the determined position being insufficient or below a quality threshold.

14. A determination method for determining a pose and shape of an introduction element within a living being, wherein the introduction element is adapted to be used by a brachytherapy apparatus for introducing a radiation source close to a target object to be treated within the living being, the determination method comprising:

determining continuously, in real-time via a position determination unit, positions of a position determination element, which is introduced into the introduction element, at different locations within the introduction element, at which the position determination element is arranged;

acquiring, via a data acquisition unit, only a fraction of the continuously determined positions of the position determination element at the different locations within the introduction element, wherein the data acquisition unit comprises a system disk configured to store the acquired fraction of determined positions for use in determining the pose and shape of the introduction element based on the acquired fraction of determined positions; and controlling, via a controller, the data acquisition unit to acquire and store the fraction of determined positions in response to the determined positions of the position determination element in real-time at the different locations within the introduction element that comprise (i) only locations within the living being and (ii) not locations outside the living being.

* * * * *